United States Patent
Rezai et al.

(10) Patent No.: US 7,715,924 B2
(45) Date of Patent: May 11, 2010

(54) ADJUSTABLE SIMULATION DEVICE AND METHOD OF USING SAME

(75) Inventors: Ali R. Rezai, Bratenahl, OH (US); Ashwini Sharan, Mt. Lauren, NJ (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1067 days.

(21) Appl. No.: 10/503,160

(22) PCT Filed: Feb. 3, 2003

(86) PCT No.: PCT/US03/03209
§ 371 (c)(1), (2), (4) Date: Feb. 3, 2005

(87) PCT Pub. No.: WO03/063949
PCT Pub. Date: Aug. 7, 2003

(65) Prior Publication Data
US 2005/0131506 A1    Jun. 16, 2005

Related U.S. Application Data

(60) Provisional application No. 60/353,687, filed on Feb. 1, 2002.

(51) Int. Cl.
*A61N 1/05* (2006.01)
(52) U.S. Cl. .................................. 607/117
(58) Field of Classification Search ............... 607/116, 607/117, 148, 152
See application file for complete search history.

(56) References Cited

U.S. PATENT DOCUMENTS

| 5,417,719 | A |   | 5/1995 | Hull et al. |
| 5,846,196 | A | * | 12/1998 | Siekmeyer et al. ........... 600/374 |
| 6,161,047 | A | * | 12/2000 | King et al. .................... 607/62 |
| 6,319,241 | B1 |  | 11/2001 | King et al. |
| 2001/0053885 | A1 |  | 12/2001 | Gielen et al. |

FOREIGN PATENT DOCUMENTS

| EP | 0 779 059 A1 | 6/1997 |
| EP | 1 048 317 A2 | 11/2000 |
| WO | WO 97/37720 A1 | 10/1997 |

OTHER PUBLICATIONS

Website: www.medtronic.com—Neurostimulators and Their Selection; Sep. 5, 2001.

* cited by examiner

*Primary Examiner*—George R Evanisko
(74) *Attorney, Agent, or Firm*—Tarolli, Sundheim, Covell & Tummino LLP

(57) ABSTRACT

A device and method for stimulating neural tissue in a patient comprising: providing a lead having opposed first and second ends defining a longitudinal axis therebetween wherein the lead having at least one electrode provided thereon for delivering electrical stimulation; implanting the lead adjacent the neural tissue; applying electrical signals to the at least one electrode to provide electrical stimulation to the neural tissue; closing all incisions made to implant the lead so that the lead is completely implanted in the patient; and adjusting, at any time after the step of closing all the incisions, the position of the lead so that it moves in a direction substantially perpendicular to the longitudinal axis of the lead.

7 Claims, 10 Drawing Sheets

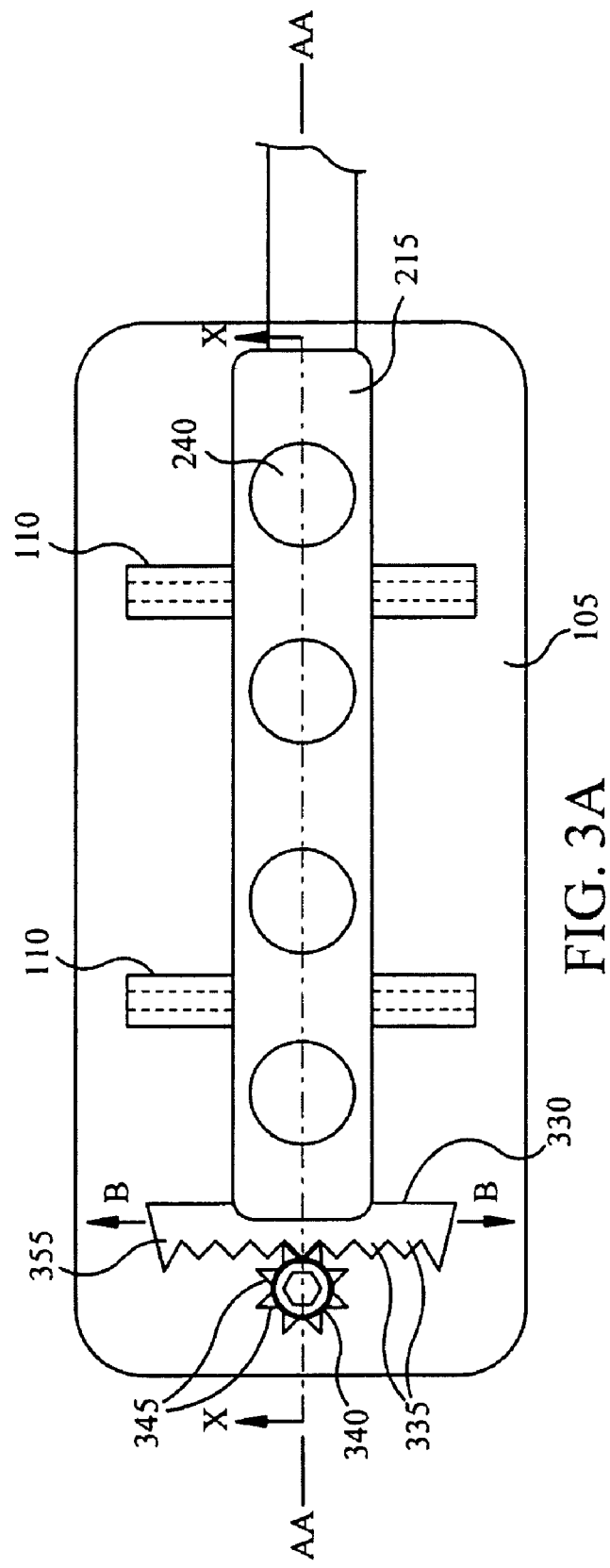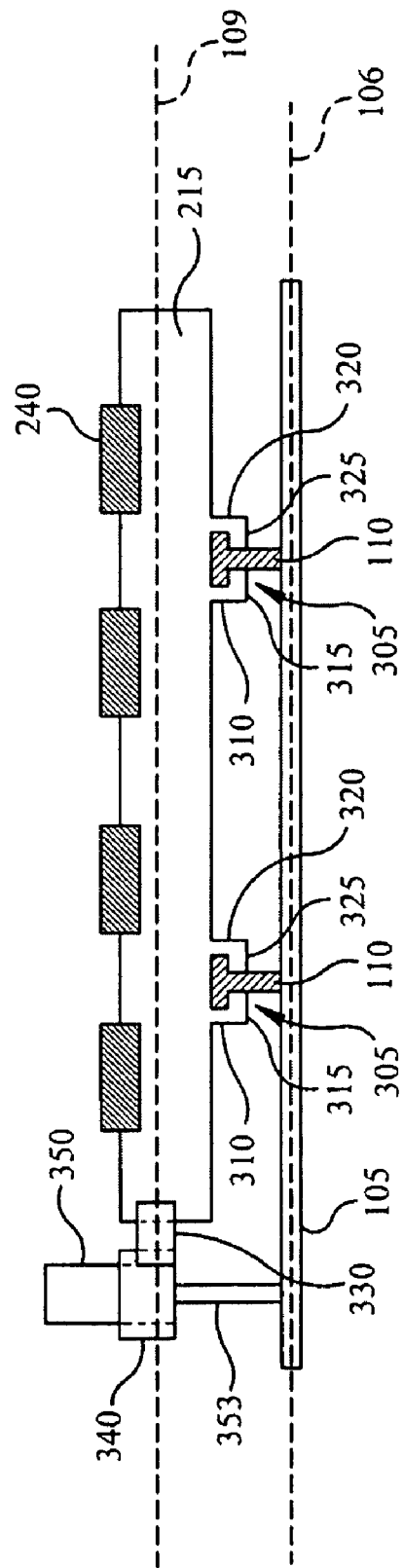
FIG. 3A
FIG. 3B

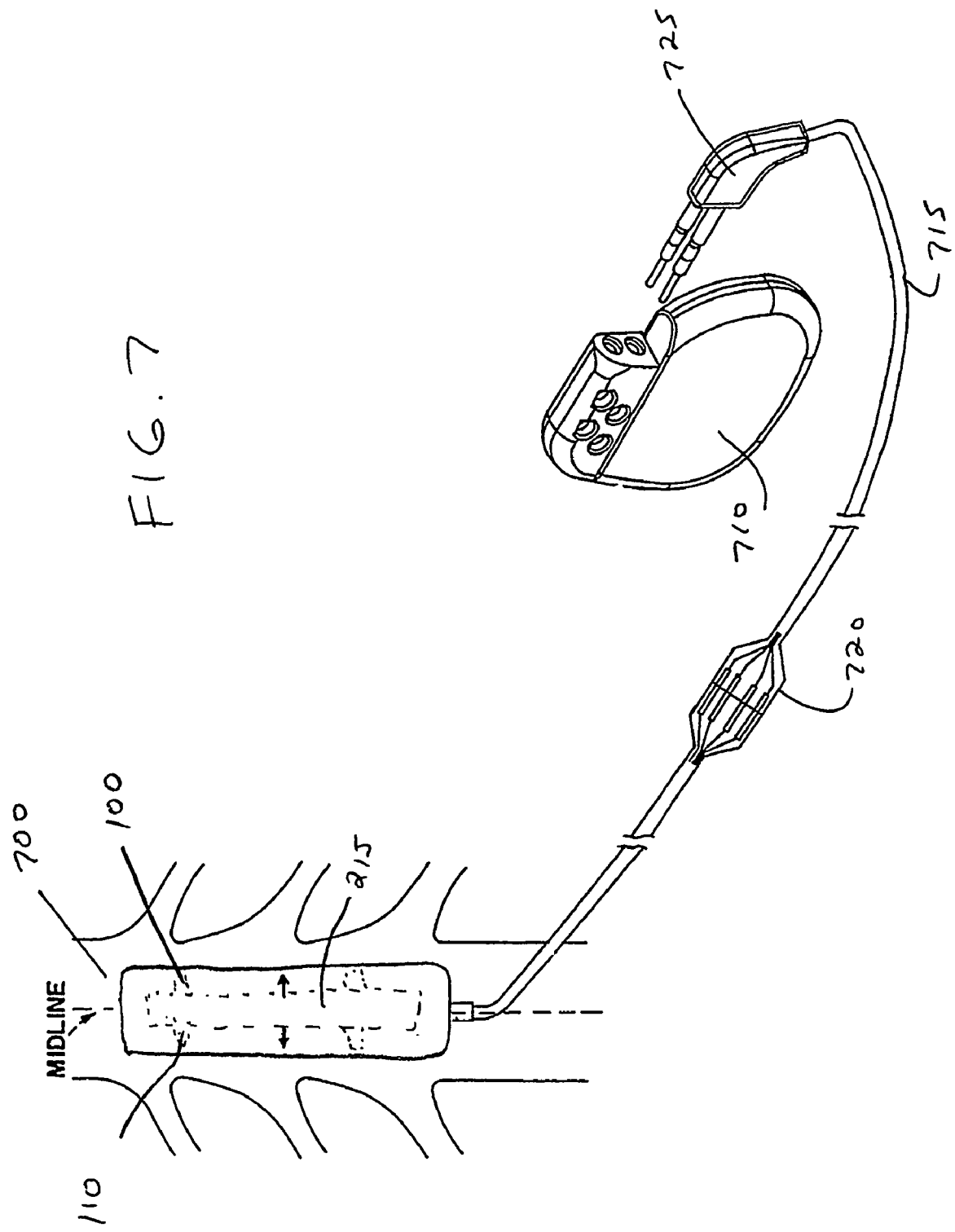

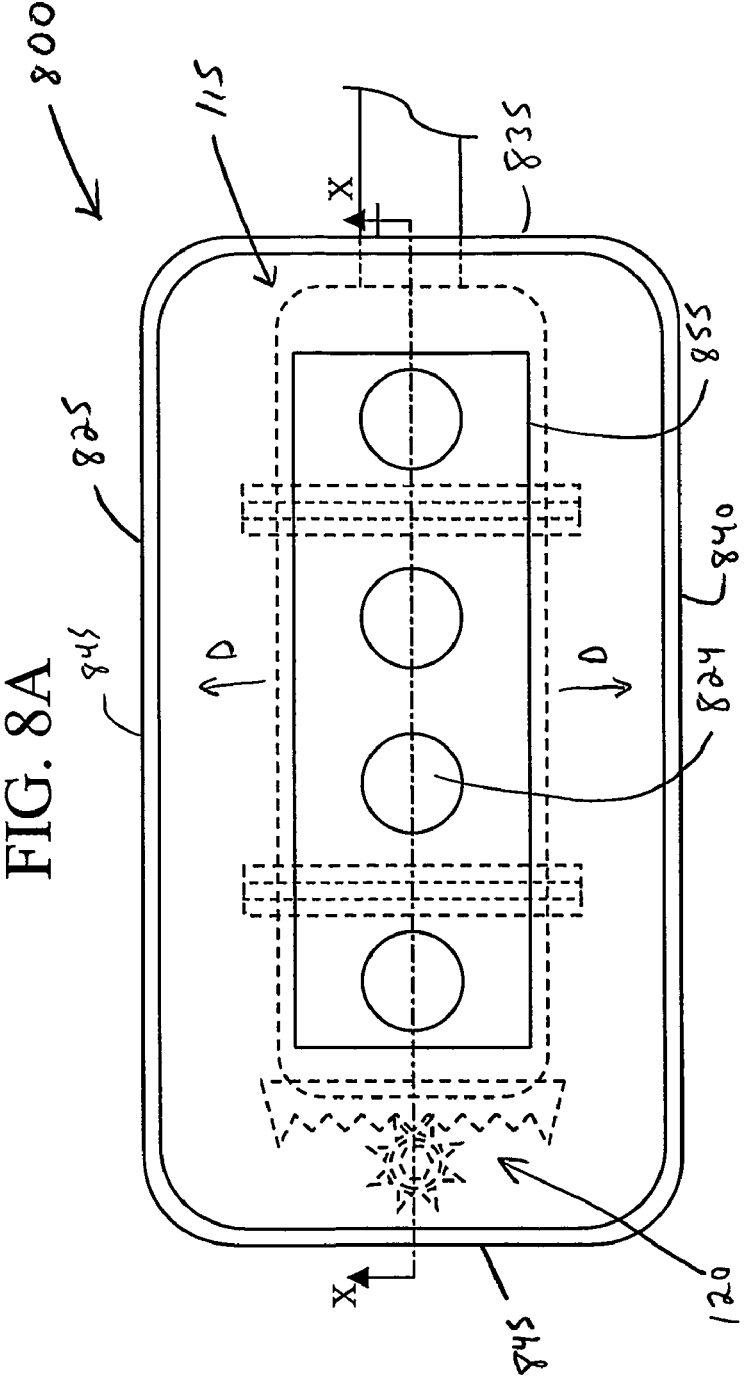

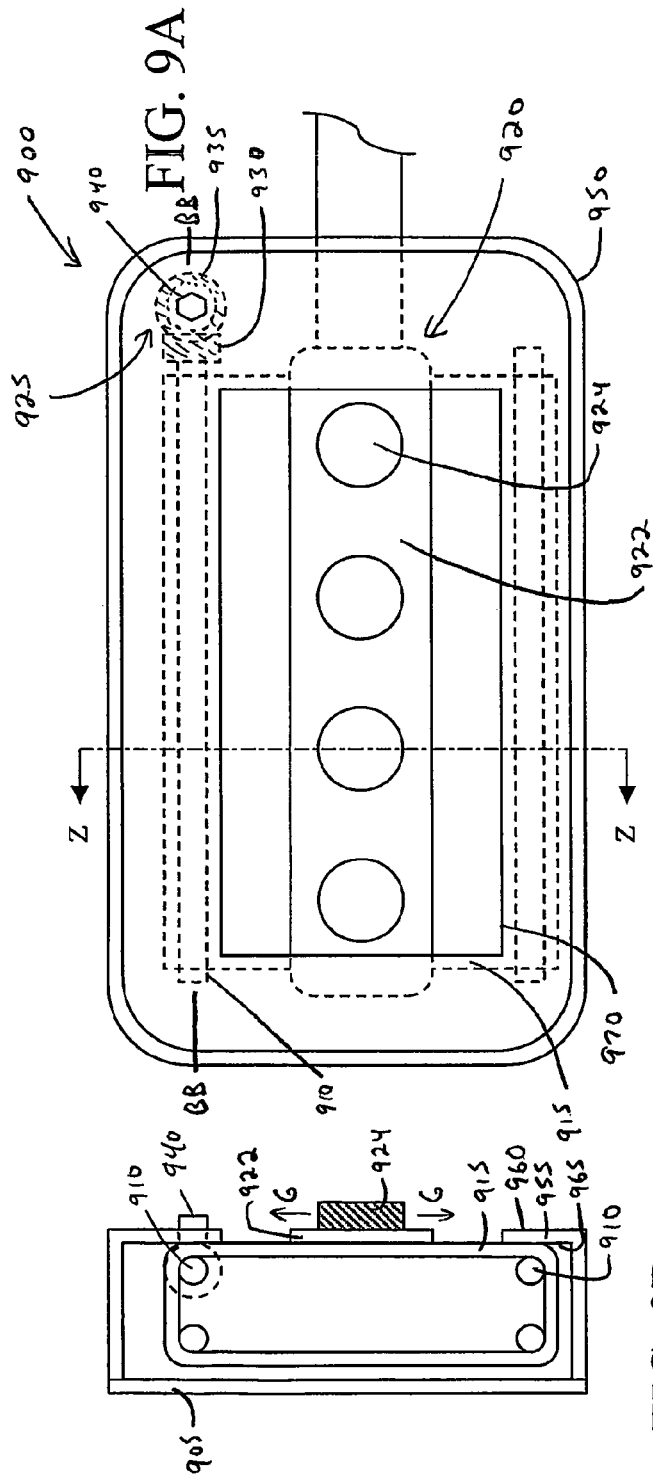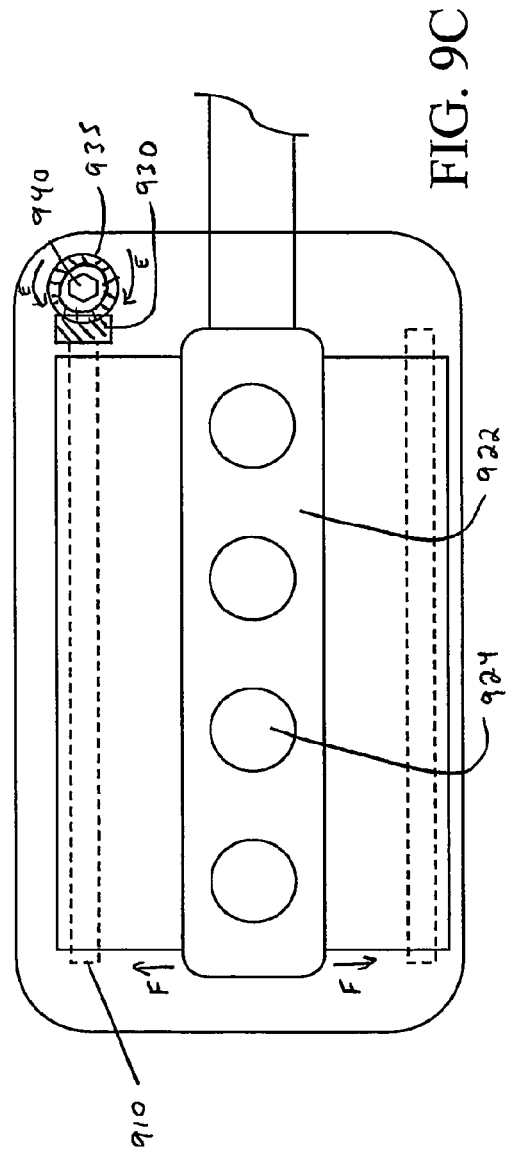

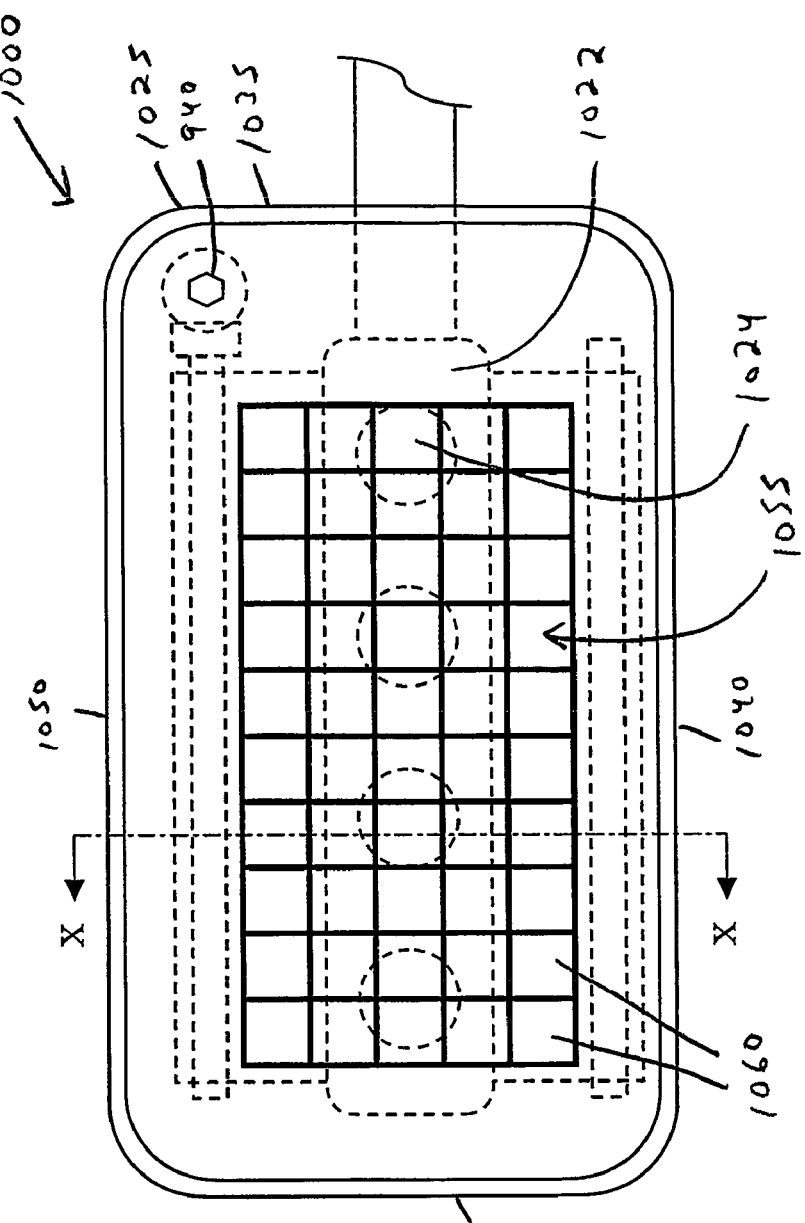
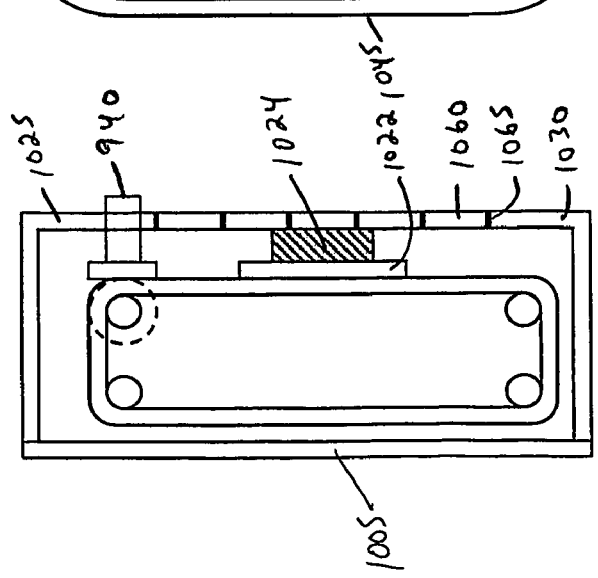

ADJUSTABLE SIMULATION DEVICE AND METHOD OF USING SAME

CROSS-REFERENCE TO RELATED APPLICATIONS

This application claims priority to U.S. Application Ser. No. 60/353,687 filed on Feb. 1, 2002. This application is incorporated herewith by reference in its entirety.

BACKGROUND OF THE INTENTION

This invention relates to a medical device and method for electrically stimulating tissue. More particularly, the invention is directed to a medical device and method for electrically stimulating the spinal cord and motor cortex.

Stimulating the spinal cord for the purpose of controlling pain was first implemented based upon the gate control theory of pain. Simply stated, the gate control theory is based on the premise that activation of large-diameter afferent nerve fibers causes an inhibition of activity in small-diameter nerve fibers. Since small-diameter fibers are involved in the perception of pain their inhibition leads to a consequent inhibition in the perception of pain. As an alternative to the gate control theory some researchers propose that, rather than a physiological gating mechanism, the activation of action potentials in the dorsal columns of the spinal cord leads to a functional blocking of signals in the collaterals of the dorsal columns which, when activated, add to the perception of pain. Under either theory the objectives and principles of spinal cord stimulation for pain control remain the same.

Pain inhibition by activation of large-diameter fibers is directly related to the area or segment of the spinal cord being stimulated. For example, to inhibit pain occurring in the foot, stimulation must activate the large-diameter fibers carrying sensory information from the foot to the spinal cord and higher brain centers. The objective of spinal cord stimulation is to induce sensory paresthesia in such a way that it broadly covers the area in which the patient feels pain. Thus, the proper location of the stimulation electrode is critical to successful pain control.

It is well known that various areas of the body are associated with the dorsal roots of nerve fibers at various spinal segments. Since the dorsal columns receive additional nerve fibers at each spinal segment, the relative position of the nerve fibers from a particular area in the periphery change from the lower spinal segments to the cervical segments. For effective pain control the electrode must be placed adjacent to the spinal column rostral to the dorsal root associated with the painful area.

It is equally well known that stimulation of the dorsal columns at different points medial to lateral will evoke paresthesia perceived as coming from different locations of the body. Additionally, the sensory fibers in the dorsal columns travel to the medulla on the same side of the cord as the peripheral area which they represent. Pain on the right side of the body is treated by placing the electrode to the right of the midline. Pain on the left side of the body is treated by placing the electrode to the left side of the midline. Bilateral pain is treated by placing the electrode on the midline or by placing electrodes on both sides of the midline. Thus, successful pain control through spinal cord stimulation depends on proper positioning of the stimulating electrode both in the longitudinal or rostral-caudal direction and in the lateral to medial direction.

Typically, implantable spinal cord stimulating leads contain multiple electrodes. Two basic styles are available. One style is the percutaneously inserted lead which is introduced through a Touhy needle. The implanting physician places the electrode in an appropriate location using fluoroscopic visualization. The procedure is done under a local anesthetic. Proper electrode placement is tested using a trial stimulation screening technique to assure that paresthesia is perceived in the affected area. An example of this type of lead is disclosed in U.S. Pat. No. 4,379,462 issued to Borkan. That lead has at least three in-line electrodes equally spaced along the distal end of the lead and is designed to be inserted so that the electrodes lie in-line along the spinal cord. Although different pairs of electrodes may be selected so that the area of stimulation may be moved longitudinally along the midline of the spinal cord, there is no provision for stimulating laterally to either or both sides of the midline unless the lead is inserted to one side of midline. In that case once the lead is placed there is no ability to stimulate other than unilaterally on the side of the midline to which the lead is placed. Should the patient later develop the need for bilateral stimulation the physician generally has three options. The physician may reposition the existing lead, implant an additional lead, or remove and replace the existing lead. Percutaneously inserted leads of this type provide focused stimulation patterns and are generally suited for unilateral pain problems. If the pain is bilateral it is often necessary to implant two leads, one on each side of the midline of the spinal cord. The leads may be connected to one pulse generator or to two pulse generators. The use of two leads can cause problems since it is difficult to maintain the relative positions of the leads with respect to one another, both in the longitudinal and lateral directions. Migration of one or both of the leads may result in a loss of paresthesia at the affected location.

The second basic spinal cord stimulation lead type are those surgically implanted through a laminotomy. An example of this type of lead is the RESUME® lead manufactured by Medtronic, Inc. of Minneapolis, Minn., the assignee of the present invention. This lead has four in-line electrodes located on an elongate paddle at the distal end of the lead. The lead is normally implanted so that the electrodes lie over the midline of the spinal cord. Because leads of this type are surgically implanted, the size of the electrodes may be made larger than those of the percutaneously implanted leads. Various electrode combinations may be selected so that the area of stimulation may be moved along the midline of the spinal cord. The lead provides a broader stimulation pattern more suitable for midline and bilateral pain problems than the percutaneously inserted lead. Since it is surgically implanted it can be sutured to prevent dislodgement and reduce lead migration. In situations where longitudinal placement of the lead over the midline of the spinal cord has not been effective to produce bilateral paresthesia this lead has been placed at an angle with respect to the midline. Once the lead has been inserted at an angle across the spinal cord it is possible, by selection of appropriate electrodes, to stimulate unilaterally on either side of the spinal cord or bilaterally across the spinal cord. However, it is no longer possible to change the stimulation pattern longitudinally along the midline. Additionally, although unilateral stimulation on either side may be provided, the stimulation areas are asymmetric or at different dorsal root levels with respect to the dorsal column. Further, since it is very difficult to maintain the precise angled placement of the lead, any migration of the lead may result in a loss of paresthesia at the affected location.

Another example of a surgically implanted lead is disclosed in U.S. Pat. No. 3,724,467 issued to Avery et al. In one embodiment the lead consists of a flat body portion at the distal end of the lead with electrodes grouped on either side of the longitudinal axis of the lead. The lead is meant to be implanted within the dura and is used for use bilateral stimulation of the spinal cord. In another embodiment the electrodes are mounted on one side of the longitudinal axis of the lead and are meant to provide stimulation to only one side of the spinal cord. In neither embodiment is there any provision for altering the stimulation pattern other than by changing the location of the lead. Thus, once this lead has been implanted there is no way to change the area of stimulation to correct for any loss of paresthesia.

In addition to the problem of lead migration as noted above it is often desirable to effect a change in the area of stimulation in order to vary the effects of paresthesia as the needs of the patient change. The problem of lead migration and the ability to effectively vary the area of stimulation both longitudinally and laterally are areas in which prior art leads have been unable to adequately address. For example, percutaneously inserted leads are difficult to anchor and have a tendency to become dislodged. Even if the initial placement is accurate, lead migration can occur which can adversely affect paresthesia. Additionally, the area in which the patient is experiencing pain can move. Percutaneous leads provide only limited means to change the area of stimulation if the lead migrates or if the needs of the patient change. This is a significant problem with respect to percutaneous leads since the electrodes must be made small enough to fit through a Touhy needle. The area of stimulation is consequently small and even a slight movement of the lead, especially laterally, can adversely affect paresthesia.

Surgically implanted leads are less affected by the problem of lead migration because the electrodes are usually larger and the lead may be stabilized by sutures. However, in instances where lead migration does occur prior art leads have allowed for changes in stimulation only longitudinally along the axis of the lead. There is no mechanism to effect a change of stimulation laterally. The same limitations apply when the needs of the patient change and it becomes desirable to alter the paresthesia.

Thus, it would be desirable to have an electrode lead that includes a position adjustment mechanism where the position of the electrode lead could be adjusted in situ after the electrode lead has been implanted into the patient.

SUMMARY OF THE INVENTION

A device and method for stimulating a spinal cord in a patient comprising: providing a lead having opposed first and second ends defining a longitudinal axis therebetween wherein the lead has at least one electrode provided thereon for delivering electrical stimulation; implanting the lead adjacent the dorsal side of a spinal cord such that the longitudinal axis of the lead is oriented substantially parallel to the midline of the spinal cord; applying electrical signals to the at least one electrode to provide electrical stimulation to the spinal cord; closing all incisions made to implant the lead so that the lead is completely implanted in the patient; and adjusting, at any time after the step of closing all the incisions, the position of the lead in situ so that it moves in a direction substantially perpendicular to the midline of the spinal cord.

A device and method for stimulating neural tissue in a patient comprising: providing a providing a lead having opposed first and second ends defining a longitudinal axis therebetween wherein the lead having at least one electrode provided thereon for delivering electrical stimulation; implanting the lead adjacent the neural tissue; applying electrical signals to the at least one electrode to provide electrical stimulation to the neural tissue; closing all incisions made to implant the lead so that the lead is completely implanted in the patient; and adjusting, at any time after the step of closing all the incisions, the position of the lead so that it moves in a direction substantially perpendicular to the longitudinal axis of the lead.

BRIEF DESCRIPTION OF THE DRAWINGS

The foregoing and other aspects of the present invention will be best appreciated with reference to the detailed description of the invention, which follows, when read in conjunction with the accompanying drawings wherein:

FIG. 3A is a plan view of one embodiment of an adjustable stimulation device 100 of the present invention without the housing cover 125;

FIG. 3B is a cross-sectional view in side elevation of the adjustable stimulation device 100 without the housing cover 125 of FIG. 3A taken along line X-X;

FIG. 7 is a partial schematic view of the spinal cord 600 of a patient with the implanted device 100 of FIG. 1 connected to a pulse generator.

FIG. 8A is a plan view of another embodiment of an adjustable stimulation device 800 according to the present invention;

FIG. 8B is a cross-sectional view in side elevation of the adjustable stimulation device 800 of FIG. 8A taken along line X-X;

FIG. 9A is a plan view of another embodiment of an adjustable stimulation device 900 according to the present invention;

FIG. 9B is a cross-sectional view in side elevation of the adjustable stimulation device 900 of FIG. 9A taken along line Z-Z;

FIG. 9C is a plan view of adjustable stimulation device 900 shown in FIG. 9A without the housing cover 925;

FIG. 10A is a plan view of another embodiment of an adjustable stimulation device 1000 according to the present invention; and FIG. 10B is a cross-sectional view in side elevation of the adjustable stimulation device 1000 of FIG. 10A taken along line X-X.

DETAILED DESCRIPTION OF THE INVENTION

Figure 1A:
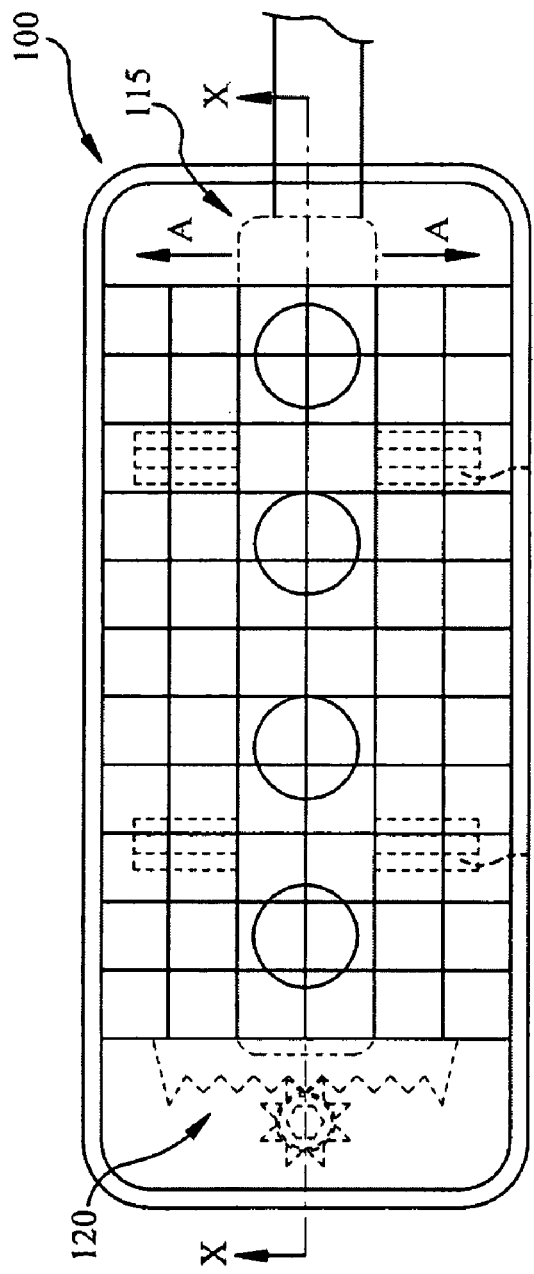
FIG. 1A is a plan view of one embodiment of an adjustable stimulation device 100 according to the present invention.

In the description that follows, like parts are indicated throughout the specification and drawings with the same reference numerals, respectively. The figures are not drawn to scale and the proportions of certain parts have been exaggerated for convenience of illustration.

Figure 1B:
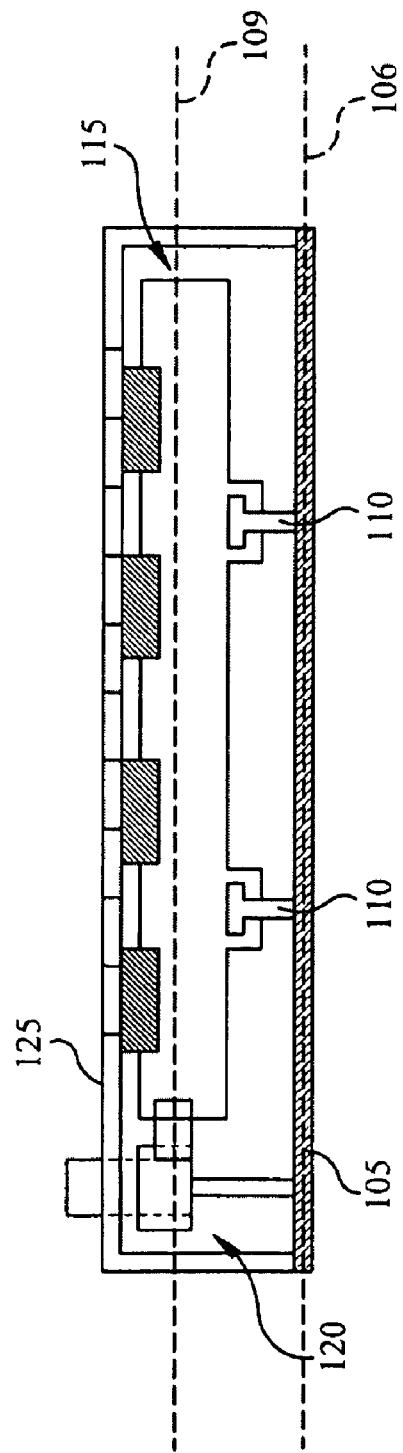
FIG. 1B is a cross-sectional view in side elevation of the adjustable stimulation device 100 of FIG. 1A taken along line X-X.

FIGS. 1A and 1B illustrate one embodiment of an adjustable stimulation device 100 according to the present invention. Device 100 comprises a housing base 105 extending along a plane 106, a pair of tongue members 110 provided on base 105, a stimulation lead assembly 115 slidably mounted to tongue members 110, a position control mechanism 120 to adjust the position of stimulation lead 115 within base 105, and a housing cover 125 releasably secured to housing base 105 to enclose the components provided therein.

Figure 2A:
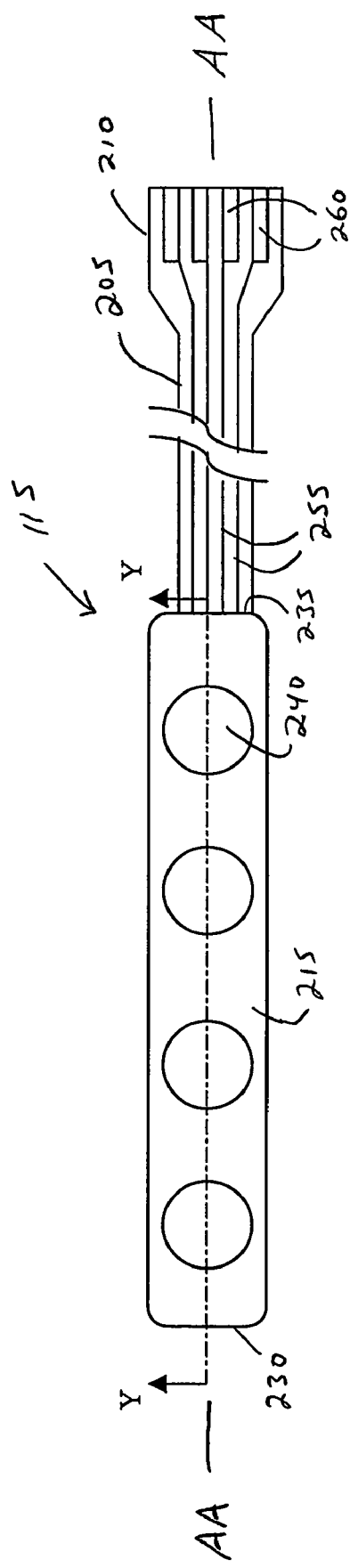
FIG. 2A is a plan view of one embodiment of a lead assembly 115 according to the present invention.
Figure 2B:
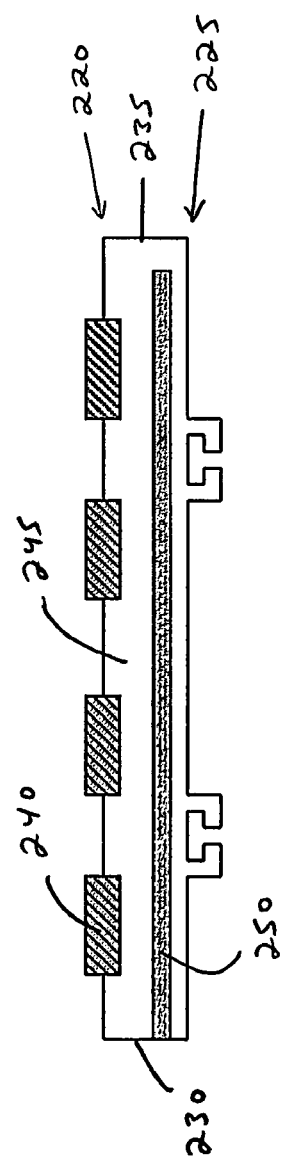
FIG. 2B is a cross-sectional view in side elevation of the lead assembly 115 of FIG. 2A taken along line Y-Y.

FIGS. 2A and 2B are top and cross-sectional side views, respectively, of lead assembly 115. Lead assembly 115 includes an insulated cable portion 205 connected at its proximal end to a flat connector 210 and at its distal end to lead body 215. Lead body 215 is an elongated body having a top portion 220, a bottom portion 225, a first end 230, and a second end 235. Lead body 215 includes an axis AA that extends longitudinally along the length of lead body 215 between first end 230 and second end 235. Although lead body 215 has a generally rectangular shape, lead body 215 may be configured in any conceivable shape.

A plurality of electrodes 240 are provided along the top portion 220 of lead body 215 to deliver electrical stimulation to targeted tissue. Although four electrodes are illustrated in the figures, it is obvious that more than four electrodes or less than four electrodes (e.g., one electrode) may be utilized. As best seen in FIG. 2B, lead body 215 is comprised of a molded silicone rubber portion 245 surrounding a mesh portion 250 made of DACRON®, a polyester material made by E. I. du Pont de Nemours & Co. Electrodes 240 are embedded within rubber portion 245 and may protrude slightly above the surface of lead body 215 in order to enhance their tissue stimulation effectiveness. As best shown in FIG. 2A, the shape and arrangement of electrodes 240 on lead body 215 are illustrated. Although electrodes 240 are circular in shape and arranged in a columnar fashion along lead body 215, it is obvious that electrodes 240 may take the form of other shapes such as oval, square, rectangular and may be arranged in any pattern such as a linear array or staggered array.

The insulated cable portion 205 of lead assembly 215 has a single lumen that encloses a plurality of conductors 255. Each conductor 255 interconnects an electrode 240 located on lead body 215 with respective stainless steel pins or terminals 260 that are molded into flat connector 210. Conductors 255 are welded to the distal ends of electrodes 240, respectively, and are crimped at ferrules (not shown) which provide strain relief The insulated cable portion 205 and flat connector 210 are made of a physiologically inert material such as silicone rubber or polyethylene. Conductors 255 are made of an appropriate electrically conductive material such as stranded stainless steel and are separately insulated with an appropriate insulating material. Preferably, they are coated with polytetrafluoroethylene (PTFE).

As stated above, lead assembly 115 is slidably mounted to a pair of tongue members 110 that may guide the movement of lead assembly 115 relative to housing base 105. As shown in FIGS. 3A and 3B where housing cover 125 is not shown to better illustrate the underlying components, tongue members 110 extend laterally along a portion of the width of base 105 substantially perpendicular to axis AA. Tongue members 110 may include any male-type structure that extends laterally along a portion of the width of base 105. Although the preferred male-type structure is a tongue member, other male-type structures are within the scope of the present invention such as a tab, rail, or track. Preferably, tongue members 110 have a T-shaped profile; however, the profile of tongue members 110 may take the form of any shape. Although tongue members 110 or any other male-type structure may be separate parts that are attached to base 105, it is possible that base 105 and tongue members 110 may be one integral part or component. If tongue members 110 are separate parts, they may be attached to base 105 by screws, rivets, or snaps. It is also possible to utilize one tongue member or three or more tongue members and still be within the scope of the present invention.

Bottom portion 225 of lead body 215 is provided with cooperating structures that engage tongue members 110 to permit lead body 215 to move along tongue members 110 in a direction perpendicular to axis AA along a plane 109 that extends parallel to the plane 106 of the base 105. In one embodiment, the cooperating structure is a T-shaped groove defined by a pair of guide shoes 305 that are projected from bottom portion 225 of lead body 215 to support lead assembly 115 on tongue members 110 as shown in FIG. 3B. Each guide shoe 305 includes a first portion 310, which is substantially perpendicular to bottom portion 225, and a second portion 315 that extends from first portion 310 in a direction towards the second end 235 of lead body 215. Preferably, second portion 315 is substantially parallel to bottom portion 225 of lead body 215 to form the T-shaped groove. Further, guide shoe 305 includes a third portion 320, which is substantially perpendicular to bottom portion 225, and a fourth portion 325 that extends from third portion 320 in a direction towards the first end 230 of lead body 215. Preferably, fourth portion 325 is substantially parallel to bottom portion 225 of lead body 215 to form the T-shaped groove.

Although guide shoes 305 may be separate parts that are attached to bottom portion 225 of lead body 215, it is preferred that guide shoes 305 and lead body 215 are one integral part. If guide shoes 305 are separate parts, they may be attached to lead body 215 by screws, rivets, or snaps. Although the preferred shape of the groove defined by guide shoes 305 is T-shaped, the grooves defined by guide shoes 305 may take the form of any shape so long as the cooperating structure (i.e., the groove) permits sliding movement of lead body 215 along tongue members 110 perpendicular to axis A and captures tongue members 110 such that lead body 215 is constrained from moving in a direction parallel to axis AA.

Alternatively, the cooperating structure may include a female-type structure disposed in bottom portion 225 of lead body 215 that extends laterally along the width of lead body 215. Although the preferred female-type structure defines a groove or channel, other female-type structures are within the scope of the present invention such as a slot or notch. Preferably, the groove or channel has a T-shaped profile; however, the groove or channel may have a simple rectangular profile or any other shape.

Alternatively, the forms of the structure disposed in or extending from lead body 215 and the cooperating structure disposed on or extending from base 105 may be reversed such that the tongue member or male-type structure may be provided on or extending from lead body 215 and the groove or female-type cooperating structure may be providing in or extending from base 105.

Although the illustrated embodiment depicts a tongue and groove sliding assembly, other sliding assemblies contemplated within the present invention include a roller/track assembly, other male/female slides, rack and pinion, and other sliding assemblies known in the art. Also, the addition of ball bearings to the slide assembly may prove helpful in minimizing friction.

As stated above, adjustable stimulation device 100 includes a position control mechanism 120 to adjust the position of lead assembly 115 relative to base 105. Position control mechanism 120 is capable of moving lead assembly 115 in the directions indicated by arrows A (see FIG. 1) which is substantially perpendicular to axis AA and along the plane 109 extending parallel to the plane 106 of the housing base 105, thereby adjusting the position of lead assembly 115 relative to housing base 105.

In one embodiment, as shown in FIGS. 3A and 3B, position control mechanism 120 includes a rack gear 330 having teeth 335 disposed thereon and a pinion gear 340 having teeth 345 disposed thereon. Rack gear 330 is coupled to lead body 215 such that movement of rack gear 330 forces movement of lead body 215. Pinion gear 340 includes a hexagonal shaped head 350 and is rotatably mounted to shaft 353 that is coupled to base 105. The teeth 335 of rack gear 330 engage and mesh with the teeth 345 of pinion gear 340 such that rotational movement of pinion gear 340 causes rack gear 330 to move laterally in the directions indicated by arrows B. Although gear rack 330 may be a separate part that is attached to lead body 215, it is possible that gear rack 330 and lead body 215 may be one integral part. If gear rack 330 is a separate part, it may be attached to lead body 215 by screws, rivets, or snaps.

Pinion gear 340 may be rotated by inserting a rigid tool (not shown), having a hexagonal socket, around the hexagonal shaped head 350 of pinion gear 340 and rotating the tool either clockwise or counter-clockwise to move rack gear 330 in either lateral direction. Rack gear 330 includes stops 355 to prevent excessive movement of rack gear 330. Alternatively, pinion gear 340 may be rotated by a small motor implanted in device 100 which runs on an electrical battery or transmitted and received radio frequency signals. Small motors may be acceptable, especially if a sequence of gears may be used to provide mechanical advantage. If such motors are used, there should be a mechanical circuit breaker to prevent excess motion. Other devices that are capable of rotating pinion gear 340 include magnetic or electromagnetic devices. Such electromechanical (i.e. motors), electromagnetic, and magnetic devices may be operated and controlled by external sources via RF signals or other telemetric systems.

Figures 4A, 4B:
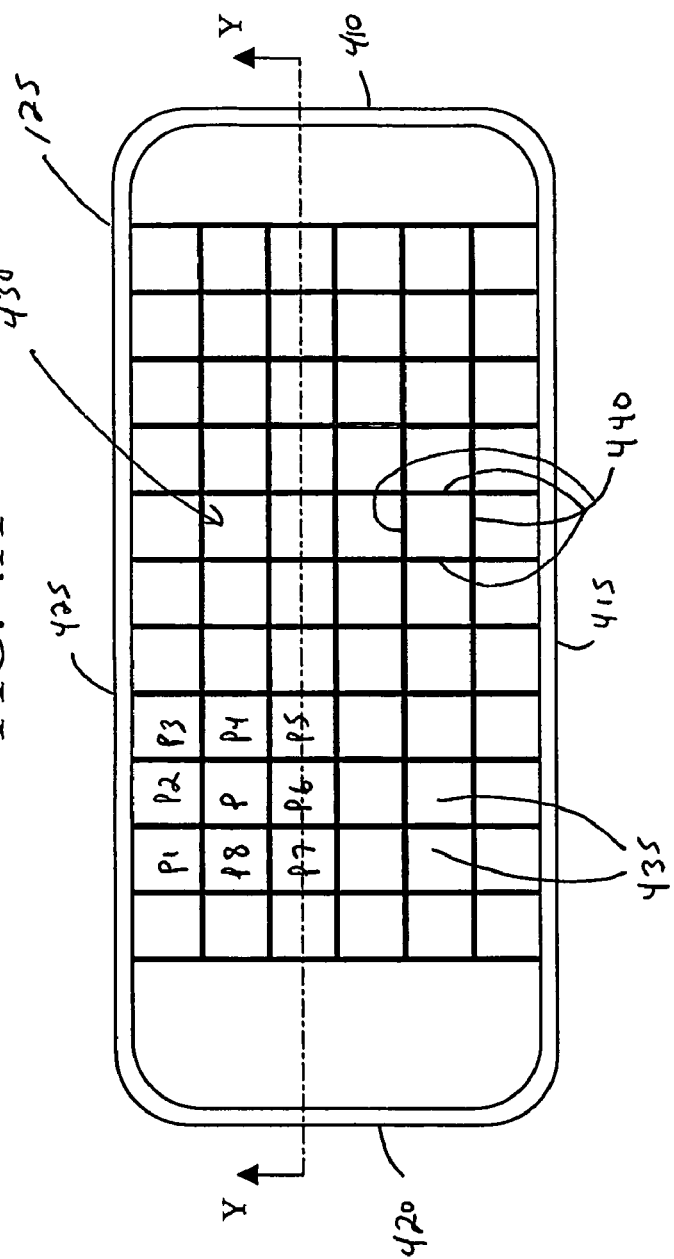
FIG. 4A is a plan view of one embodiment of a housing cover 125 of the present invention.
FIG. 4B is a cross-sectional view in side elevation of the housing cover 125 of FIG. 4A taken along line Y-Y.

As stated above, housing cover 125 engages housing base 105 and encloses the components provided therebetween. As shown in FIGS. 4A and 4B, housing cover 125 includes a top wall 405 and side walls 410, 415, 420, and 425. Top wall 405 of housing cover 125 includes a grid 430 comprised of a plurality of electrically conductive panels 435 surrounded by electrically insulated frames 440 wherein each frame 440 prevents electrical continuity between adjacent panels 435. For example, when only one panel (see panel P in FIG. 4A) is electrically active, the adjacent panels (see panels P1-P8) are electrically inactive because the frame surrounding panel P prevents the electrical current from traveling to the adjacent panels.

Figure 5A:
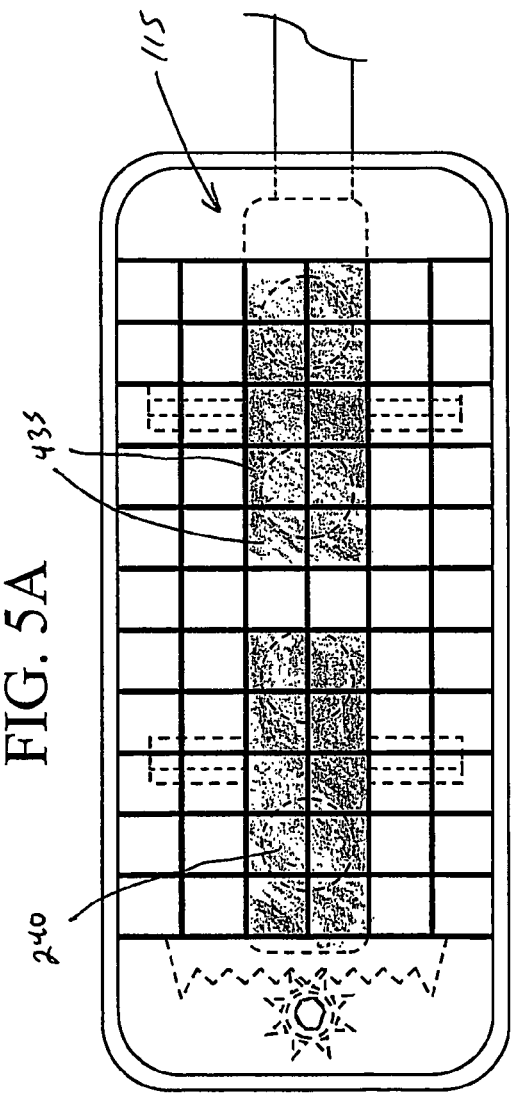
FIG. 5A is a plan view of adjustable stimulation device 100 illustrating the electrically active panels 435 when lead assembly 115 is centered (panels 435 are shaded)
Figure 5B:
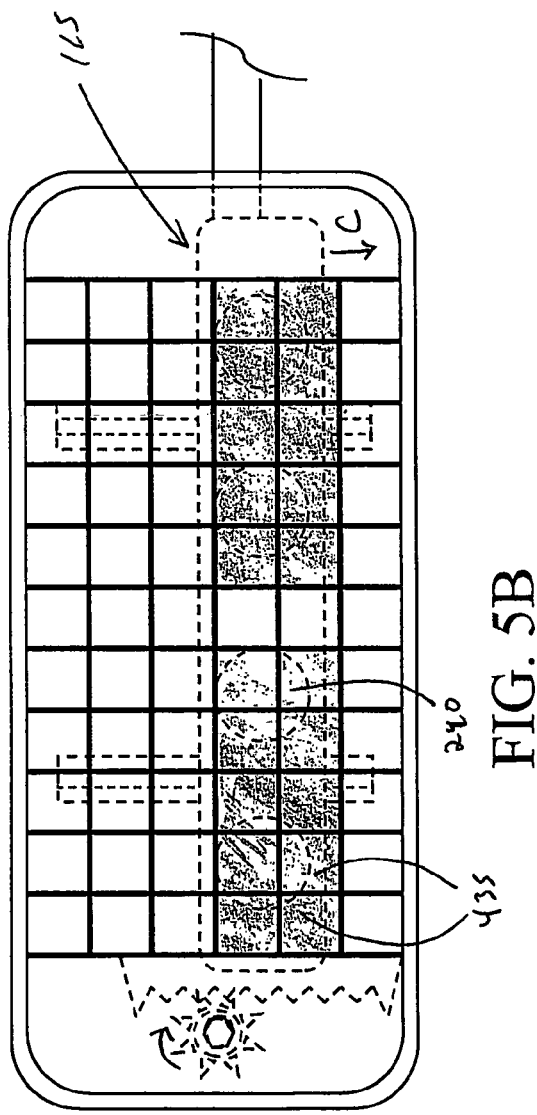
FIG. 5B is a plan view of adjustable stimulation device 100 illustrating the electrically active panels 435 when lead assembly 115 is moved in the direction indicated by arrow C (panels 435 are shaded)

Each electrically conductive panel 435 includes a top surface 445 and a bottom surface 450. When housing cover 125 is engaged with housing base 105, the bottom surface 450 of at least a portion of panels 435 (see FIG. 5A where panels 435 are shaded) come into contact or at least close enough proximity with the top surface of electrodes 240 (collectively referred to as "electrical contact") such that when electrodes 240 are electrically active, the panels 435 that are in electrical contact with electrodes 240 are electrically active. Accordingly, when lead body 215 is moved to a new position (e.g., when pinion gear 340 is rotated clockwise, rack gear 330 moves in the direction indicated by arrow C), only the panels 435 that are in electrical contact with electrodes 240 remain electrically active (see FIG. 5B where panels 435 are shaded), while panels 435 that are no longer in electrical contact with electrodes 240 return to being electrically inactive.

Further, housing cover 125 includes an opening to permit the head 350 of pinion gear 340 to protrude through the top wall 405 to permit an operator to access and rotate the head 350 of pinion gear 340 with a tool without having to access the internal components of device 100. Alternatively, housing cover 125 may include an access panel or other closeable-type opening to permit access to pinion gear 340 if the head does not protrude through the top wall 405.

The housing base 105 and cover 125 are constructed of any material such as a physiologically inert plastic. Panels 435 are constructed of any electrically conductive material such as platinum-iridium, stainless steel, or titanium. The electrically insulated frames 440 are constructed of a material similar to the housing components or any other insulating material such as silicone rubber or polyethylene.

Although housing base 105 and housing cover 125 may be separate part or components, it is possible that housing base 105 and housing cover 125 may be of unitary construction.

Although the invention will be described herein with reference to spinal cord stimulation (SCS) procedures, Cortical Surface Stimulation, and or Deep Brain Stimulation (DBS) it will be recognized that the invention finds utility in applications other than SCS procedures, including other applications such as Peripheral Nerve or Ganglia Stimulation, Intra-Spinal Stimulation, Sacral Root Stimulation, or Intraventricular Cerebral Stimulation. In addition, the invention finds applicability to SCS procedures where the lead is placed in the intrathecal or subdural space. The present invention may also be utilized to provide stimulation of various muscles of the body such as the cardiac muscle.

Figure 6:
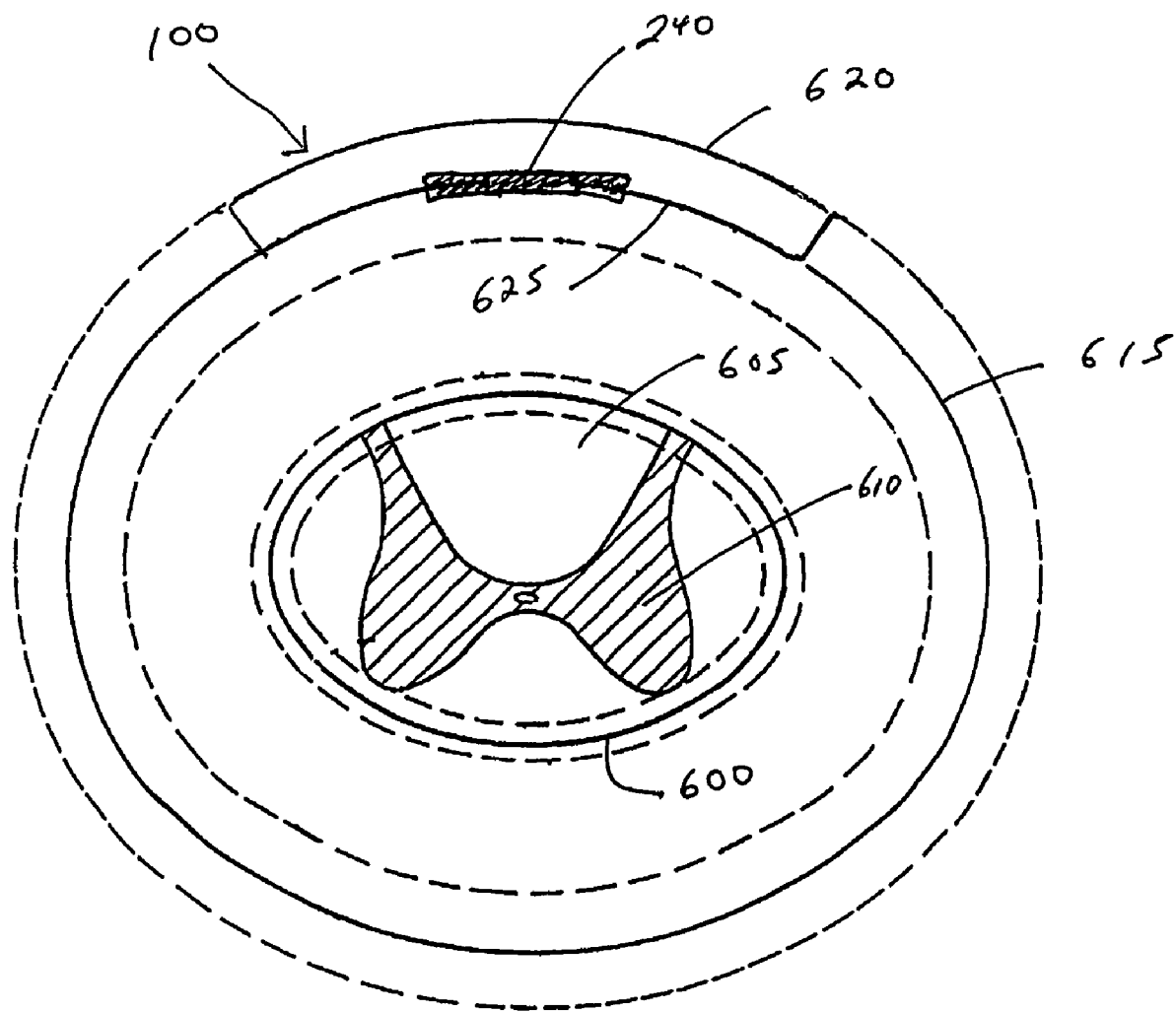
FIG. 6 is a cross-sectional view of a spinal cord 600 at spinal bone level at T-6 having a device 100 implanted thereon.

FIG. 6 is a cross-sectional view of spinal cord 600 at spinal bone level T-6 having device 100 implanted therein in accordance with one embodiment of the present invention. Spinal cord 600 generally includes white matter 605, grey matter 610, and a surrounding dural sack 615. FIG. 6 shows the average width, height and spacing of tissue components at vertebral bone level T6. The dashed lines in these figures indicate distances of one standard deviation from the mean. See J. Holsheimer et al., "MR Assessment of the Normal Position of the Spinal Cord in the Spinal Cannal," Am. J. Neuroradiology, Vol. 15, pp. 951-959 (1994).

As shown, device 100 is implanted in the epidural space outside of dural sack 615, but may alternatively be implanted in the intrathecal spinal space or subcortically beneath dural sack 615. In this embodiment, device 100 has a curved shape to match the shape of dural sack 615. The curvature may be matched to each spinal level or may be a general shape to approximately match all levels of spinal cord. Alternatively, device 100 may be flat such that it "grips" the vertebral bone on its dorsal edges and is less prone to migration or rotation. Device 100 has a dorsal side 620 away from spinal cord 600 and a ventral side 625 facing spinal cord 600.

As shown in FIG. 7, device 100 is adapted to be implanted in a human patient along the dorsal side of the spinal column 700. A detailed description of the method of stimulate the spinal cord is described in a chapter entitled "Spinal Cord Stimulation for Pain Relief" in the text "Neurosurgery" by Giancarlo Barolet and Ashwini Sharan, edited by Wilkins and Rengacharey, Edition 3, (2003), which is hereby incorporated by reference in its entirety herein. Device 100 is first implanted such that the longitudinal axis AA of lead body 215 is oriented substantially parallel to the midline of said spinal cord. This aligns electrodes 240 on lead assembly 115 substantially parallel to the midline of spinal cord 600. Each electrode is independently selectable so that a variety of stimulation patterns may be selected by providing stimulation signals to two or more of electrodes 240. The stimulation signals or pulses are provided by an external pulse generator during an initial screening procedure to determine a correct lead placement and electrode combination that will adequately supply paresthesia to the desired location. During the screening process, various electrode combinations are tested until the right combination is achieved.

After the screening process has been completed and device 100 is properly anchored in place, device 100 is connected to an implanted pulse generator 710 by a lead extension 715 as shown in FIG. 7. Lead extension 715 has a flat connector 720 at its distal end which connects to flat connector 210 and has a plug-in connector 725 at its proximal end which connects to pulse generator 710. Pulse generator 710 may be a fully implanted system such as the "ITREL II" pulse generator available from Medtronic. Inc. or may employ a partially implanted radio-frequency system such as the "XTREL" system also available from Medtronic, Inc.

In use, device 100 is designed to be implanted in the epidural space after the dura has been exposed by a partial laminectomy. Although the invention will be described primarily in connection with its implantation in the epidural space along the dorsal column for use in stimulating the spinal cord as a method of treating pain, it should be noted that the electrode may be used for any spinal cord stimulation application such as stimulation to induce motor function or to inhibit spasticity. When used for such other applications, device 100 may be implanted laterally or on the ventral side of the spinal column. Device 100 is also suitable for use in applications other than spinal cord stimulation such as stimulation of peripheral nerves.

Once the stimulation system including device 100 has been implanted and all the incisions made to implant device 100 have been closed so that said lead is completely implanted in said patient, device 100 provides the flexibility to make modifications to the area of paresthesia should the needs of the patient change or should there be any lead migration. This may be accomplished using an adjustment procedure described herein. First, the surgeon identifies the exact location of the hexegonal shaped head 350 of pinion gear 340 using CT or MRI equipment. Once the surgeon identifies the location of the hexegonal shaped head 350 of pinion gear 340, the surgeon makes in opening in the back of the patient to access the the hexegonal shaped head 350 of pinion gear 340. Once the hexegonal shaped head 350 of pinion gear 340 is accessible, the surgeon passes a rigid tool (not shown) having a hexagonal-shaped socket through the patient's skin and engages hexegonal shaped head 350 of pinion gear 340. The surgeon may then rotate the pinion gear 340 clockwise or counterclockwise using tool to actuate rack 330 back and forth thereby causing lead body 215 (and electrodes 240 provided thereon) to move in a direction substantially perpendicular to the midline of the spinal cord 600. Advantageously, electrodes 240 may be repositioned relative to the spinal cord 600 such that the targeted neural tissue is stimulated with optimal efficacy. Thus, device 100 provides a substantial amount of flexibility in achieving a stimulation pattern which is moveable laterally along the spinal column and which is effective in supplying paresthesia even if the area of pain changes or there is migration of the lead.

FIGS. 8A and 8B illustrate another embodiment of an adjustable stimulation device 800 according to the present invention. Adjustable stimulation device 800 includes a similar base 105, tongue members 110, and position control mechanism 120 as shown and described above. Lead assembly 815 is also similar to lead assembly 115 as shown and described and includes a lead body 820 and a plurality of electrodes 824 disposed thereon., except that the width of lead body 820 may be larger.

In this embodiment, housing cover 825 also engages housing base 105 and encloses the components provided therebetween. As shown in FIGS. 8A and 8B, housing cover 825 includes a top wall 830 having a top surface 832 and bottom surface 834, and side walls 835, 840, 845, and 850. Housing cover 825 includes an aperture 855 in top wall 830 to expose a portion of lead body 820 and electrodes 824 to tissue. When housing cover 825 is engaged with housing base 105, the bottom surface 834 of at least a portion of top wall 830 overlaps at least a portion of the perimeter of lead body 820 and comes into contact with the top surface of lead body 820 to thereby prevent fluid or tissue from entering device 800. Although the bottom surface 834 of top wall 830 comes into contact with the top surface of lead body 820, the friction between the two surfaces is low enough to permit lead body 820 to move relative to top wall 830 of housing cover 825, but large enough to prevent fluid or tissue from entering device 800. Preferably, the width (w) of aperture 830 is large enough so that lead body 820 (and electrodes 824) can move laterally as indicated by arrows D with respect to base 105. Optionally, electrodes 824 may protrude slightly above the surface of top wall 830 in order to enhance their tissue stimulation effectiveness.

Device 800 is implanted and operates in a similar fashion as device 100 shown and described above. Once the stimulation system including device 800 has been implanted, device 800 provides the flexibility to make modifications to the area of paresthesia should the needs of the patient change or should there be any lead migration. This may be accomplished using an adjustment procedure similar to the procedure described above.

Further, housing cover 825 includes an opening to permit the head 350 of pinion gear 340 to protrude through the top wall 830 to permit an operator to access and rotate the head 350 of pinion gear 340 with a tool without having to access the internal components of device 800. Alternatively, housing cover 825 may include an access panel or other closeable-type opening to permit access to pinion gear 340 if the head does not protrude through the top wall 830.

FIGS. 9A, 9B, and 9C illustrate another embodiment of an adjustable stimulation device 900 according to the present invention. Device 900 comprises a housing base 905 and a plurality of rollers 910 provided on base 905. Rollers 910 extend parallel to the surface of base 905 defining axis BB. A continuous belt 915 or other tensile member is provided in rolling engagement with the outside diameter of rollers 910. A stimulation lead assembly 920 is coupled to belt 915 such that movement of belt 915 causes lead assembly 920 to move. Lead assembly 920 is similar to lead assembly 215 described above and includes a lead body 922 and a plurality of electrodes 924 disposed thereon.

A position control mechanism 925 is provided to adjust the position of stimulation lead 920 within base 905. Position control mechanism 925 includes a first bevel gear 930 that is coupled to and shares the same axis as one of the rollers 910. Position control mechanism 925 further includes a second bevel gear 935 having an axis of rotation in a different plane oriented ninety degrees from axis BB of first bevel gear 930. Second bevel gear 935 includes a hexagonal shaped head 940 and is rotatably mounted to shaft 945 that is coupled to base 905. The teeth of first bevel gear 930 engage and mesh with the teeth of second bevel gear 935 such that rotational movement of first bevel gear 930 as indicated by arrows E causes second bevel gear 935 to rotate in a plane perpendicular to rotation of first bevel gear 930 thereby causing roller 910 and belt 915 (and lead body 922) to move in the directions indicated by arrows F.

Second bevel gear 935 may be rotated by inserting a rigid tool (not shown), having a hexagonal socket, around the hexagonal shaped head 938 of second bevel gear 935 and rotating the tool either clockwise or counter-clockwise to rotate first bevel gear 930 thereby moving belt 915 in either lateral direction. Alternatively, second bevel gear 935 may be rotated by a small motor implanted in device 900 which runs on an electrical battery or transmitted and received radio frequency signals. Small motors may be acceptable, especially if a sequence of gears may be used to provide mechanical advantage. If such motors are used, there should be a mechanical circuit breaker to prevent excess motion. Other devices that are capable of rotating pinion gear 340 include magnetic or electromagnetic devices. Such electromechanical (i.e. motors), electromagnetic, and magnetic devices may be operated and controlled by external sources via RF signals or other telemetric systems.

In this embodiment, a housing cover 950 is provided to mate with housing base 905 and enclose the components provided therebetween. As shown in FIGS. 9A, 9B, and 9C, housing cover 950 includes a top wall 955 having a top surface 960 and bottom surface 965. Housing cover 950 includes an aperture 970 in top wall 955 to expose a portion of lead body 922 and electrodes 924 to tissue. When housing cover 950 is engaged with housing base 905, the bottom surface 965 of at least a portion of top wall 955 overlaps at least a portion of the perimeter of lead body 922 and comes into contact with the top surface of lead body 922 to thereby prevent fluid or tissue from entering device 900. Although the bottom surface 965 of top wall 955 comes into contact with the top surface of lead body 922, the friction between the two surfaces is low enough to permit lead body 922 to move relative to top wall 955 of housing cover 950, but large enough to prevent fluid or tissue from entering device 900. Preferably, the width (w) of aperture 970 is large enough so that lead body 922 (and electrodes 924) can move laterally as indicated by arrows G with respect to base 905. Optionally, electrodes 924 may protrude slightly above the surface of top wall 830 in order to enhance their tissue stimulation effectiveness.

Further, housing cover 950 includes an opening to permit the head 940 of second bevel gear 935 to protrude through the top wall 955 to permit an operator to access and rotate the head 940 of second bevel gear 935 with a tool without having to access the internal components of device 900. Alternatively, housing cover 950 may include an access panel or other closeable-type opening to permit access to second bevel gear 935 if the head does not protrude through the top wall 955.

Device 900 is implanted and operates in a similar fashion as device 100 shown and described above. Once the stimulation system including device 900 has been implanted, device 900 provides the flexibility to make modifications to the area of paresthesia should the needs of the patient change or should there be any lead migration. This may be accomplished using an adjustment procedure similar to the procedure described above.

FIGS. 10A and 10B illustrate yet another embodiment of an adjustable stimulation device 1000 according to the present invention. Device 1000 comprises the same components as device 900 shown and described above, but includes a housing cover 1025 different from housing cover 950 of device 900. Stimulation lead assembly 1020 is similar to lead assembly 915 described above and includes a lead body 1022 and a plurality of electrodes 1024 disposed thereon.

As stated above, housing cover 1025 engages housing base 1005 and encloses the components provided therebetween. As shown in FIGS. 10A and 10B, housing cover 1025 includes a top wall 1030 and side walls 1035, 1040, 1045, and 1050. Top wall 1030 of housing cover 1025 includes a grid 1055 comprised of a plurality of electrically conductive panels 1060 surrounded by electrically insulated frames 1065 wherein each frame 1065 prevents electrical continuity between adjacent panels 1060. The relationship between the electrically conductive panels 1060 and electrodes 1024 disposed on lead body 1022 is similar to the electrically conductive panels 435 and electrodes 240 disposed on lead body 215 described above for device 100.

Further, housing cover 1025 includes an opening to permit the head 940 of second bevel gear 935 to protrude through the top wall 1030 to permit an operator to access and rotate the head 940 of second bevel gear 935 with a tool without having to access the internal components of device 1000. Alternatively, housing cover 1025 may include an access panel or other closeable-type opening to permit access to second bevel gear 935 if the head does not protrude through the top wall 1030.

Device 1000 is implanted and operates in a similar fashion as device 100 shown and described above. Once the stimulation system including device 900 has been implanted, device 900 provides the flexibility to make modifications to the area of paresthesia should the needs of the patient change or should there be any lead migration. This may be accomplished using an adjustment procedure similar to the procedure described above.

As stated above, the position control mechanisms may be actuated by electromechanical, electromagnetic, or magnetic devices that may be operated and controlled by external sources via RF signals or other telemetric systems. Further, the individual electrodes on the lead may be adjusted post-operatively by turning them on/off, adjusting the voltage, adjusting the frequency, and adjusting other electrical signal parameters through the use of telemetry, RF signals, or other systems known in the art. Also, if chemical stimulation is also provided, the ports may be opened or closed or the amount of drug being delivered may be adjusted post-operatively through the use of telemetry, RF signals, or other systems known in the art. Systems for communicating with implantable medical devices are disclosed, for example, in U.S. Application Serial No. 2002/0082665 entitled System And Method Of Communicating Between An Implantable Medical Device And A Remote Computer System Or Health Care Provider and U.S. Application Serial No. 2001/0012955 entitled Method And Apparatus For Communicating With An Implantable Medical Device, and U.S. Pat. No. 6,201,993 entitled Medical Device Telemetry Receiver Having Improved Noise Discrimination, and are incorporated by reference in their entireties herein for their teachings.

The system may optionally include one or more sensors to provide closed-loop feedback control of the treatment therapy and/or electrode positioning. One or more sensors are attached to or implanted into a portion of a patient's body suitable for detecting a physical and/or chemical symptom or an important related symptom of the body.

The present invention may also be implemented alone or in combination with a drug delivery system to provide chemical stimulation utilizing a drug, pharmaceutical, or therapeutic agent. In this embodiment, a pump and catheter is provided either alone or in combination with the signal generator and the electrode. The pump may be implanted below the skin of a patient and has a port into which a hypodermic needle can be inserted through the skin to inject a quantity of a liquid agent, such as a drug, pharmaceutical, or therapeutic agent. The liquid agent is delivered from pump through a catheter port into a catheter. The catheter is positioned to deliver the liquid agent to a predetermined region of the brain.

Optionally, the present invention may incorporate a closed-loop feedback system to provide automatic adjustment of the electrical and/or chemical stimulation therapy. The system may incorporate a sensor to provide feedback to provide enhanced results. Sensor can be used with a closed loop feedback system in order to automatically determine the level of electrical and/or chemical stimulation necessary to provide the desired treatment. Sensor may be implanted into a portion of a patient's body suitable for detecting symptoms of the disorder being treated. Sensor is adapted to sense an attribute of the symptom to be controlled or an important related symptom. Sensors suitable for this purpose may include, for example, those disclosed in U.S. Pat. No. 5,711,316, which is incorporated herein by reference in its entirety. In cases where the attribute of the symptom is the electrical activity of the brain, stimulating electrodes may be intermittently used to record electrical activity. Alternatively, one or more electrodes implanted within the brain may serve as a sensor or a recording electrode. When necessary, these sensing or recording electrodes may deliver stimulation therapy to the predetermined region of the brain. The output of an external feedback sensor may communicate with the implanted pulse generator through a telemetry down-link.

The operator preferably may also selectively adjust the energy, amplitude or pulse parameters delivered to each electrode. The selective control over each electrode may be achieved by employing a programmer which is coupled via a conductor to a telemetry antenna. The programmer is capable of sending signals via the telemetry antenna to control the electrical signal delivered to the electrodes and to control the actuator system. The system permits attending medical personnel to select the various pulse output options after implant using telemetry communications. While the preferred system employs fully implanted elements, systems employing partially implanted generators and radio-frequency coupling may also be used in the practice of the present invention. Advantageously, the present invention allows the locus of excitation to be selectively adjusted and/or steered to precisely target portions of the brain to achieve the desired treatment therapy. The steering may be accomplished in the manner described in U.S. Pat. No. 5,713,922 which is incorporated herein by reference in its entirety.

Furthermore, it is understood that one ordinarily skilled in the art can appreciate the ability to select and power individual electrodes independently from other electrodes in order to stimulate the desired target region and to obtain desired directional properties. Specifically, this ability to control the energizing of electrodes enables a physician to focus (i.e. direct) an electrical field around the chosen powered electrode thus pinpointing the stimulation area. Additionally, the shape of the electric field will vary corresponding to the power applied, the number and arrangement of electrodes, and particular shapes and sizes chosen for the electrodes. Also, each electrode may be selectively powered as an anode, cathode or neither.

From the foregoing detailed description of specific embodiments of the invention, it should be apparent that a neurological stimulation lead for spinal cord stimulation has been disclosed. Although several particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. For instance, the choice of materials or variations in the shape of the lead body or electrodes or electrode array are believed to be a matter of routine for a person of ordinary skill in the art with knowledge of the embodiments disclosed herein. Likewise, although the embodiments disclosed relate primarily to spinal cord stimulation for treatment of pain, the stimulation lead disclosed herein could be used for other applications such as nerve stimulation for control of motor function.

What is claimed is:

1. An adjustable stimulation device comprising:
   an elongated lead body having opposed first and second ends defining a longitudinal axis therebetween, said lead body having at least one electrode for delivering electrical stimulation to targeted tissue;
   a position control mechanism for permitting adjustment of the position of said lead body in a direction substantially perpendicular to said longitudinal axis of said lead body;
   a housing base extending along a plane parallel to said longitudinal axis and having a structure for guiding the movement of said lead body relative to said housing base;
   said lead body having a cooperating structure that is in continuous sliding engagement with said housing base structure during adjustment of the position of said lead body in a direction substantially perpendicular to said longitudinal axis of said lead body and along a plane substantially parallel to said housing base plane,
   wherein said cooperating structure defines a groove extending substantially perpendicular to said longitudinal axis of said lead body and said structure comprises a tongue member extending from said housing base that engages said groove,
   wherein said cooperating structure further comprises a pair of guide shoes where each of said guide shoes includes a first portion that extends from said bottom portion in a direction substantially perpendicular to said bottom portion and a second portion that extends from said first portion in a direction substantially parallel to and spaced from said bottom portion.

2. The device of claim 1, wherein said groove defines a T-shaped profile and said tongue member defines a corresponding T-shaped profile.

3. An adjustable stimulation device comprising:
   an elongated lead body having opposed first and second ends defining a longitudinal axis therebetween, said lead body having at least one electrode for delivering electrical stimulation to targeted tissue;
   a position control mechanism for permitting adjustment of the position of said lead body in a direction substantially perpendicular to said longitudinal axis of said lead body;
   a housing base extending along a plane parallel to said longitudinal axis and having a structure for guiding the movement of said lead body relative to said housing base;
   said lead body having a cooperating structure that is in continuous sliding engagement with said housing base structure during adjustment of the position of said lead body in a direction substantially perpendicular to said longitudinal axis of said lead body and along a plane substantially parallel to said housing base plane, wherein said structure defines a track disposed in said housing base and said cooperating structure comprises a rail extending substantially perpendicular to said longitudinal axis of said lead body that engages said channel.

4. The device of claim 3, wherein said position control mechanism comprises a rack gear coupled to said lead body in a substantially perpendicular orientation and a pinion gear engaged with said rack gear such that rotation of said pinion gear causes rack gear to move in a direction only perpendicular to said longitudinal axis.

5. The device of claim 4, wherein said pinion gear includes a hexagonal recess for received a hexagonal-tipped needle.

6. An adjustable stimulation device comprising:
an elongated lead body having opposed first and second ends defining a longitudinal axis therebetween, said lead body having at least one electrode for delivering electrical stimulation to targeted tissue;
a position control mechanism for permitting adjustment of the position of said lead body in a direction substantially perpendicular to said longitudinal axis of said lead body;
a housing base extending along a plane parallel to said longitudinal axis and having a structure for guiding the movement of said lead body relative to said housing base; and
a housing cover releasably secured to said housing base, said housing cover comprising a plurality of electrically conductive panels having a top surface and a bottom surface, each of said plurality of electrically conductive panels is surrounded by an electrically insulated frame,
said lead body having a cooperating structure that is in continuous sliding engagement with said housing base structure during adjustment of the position of said lead body in a direction substantially perpendicular to said longitudinal axis of said lead body and along a plane substantially parallel to said housing base plane.

7. The device of claim 6, wherein a top surface of said electrode in electrical contact with said bottom surface f at least a portion of said plurality of electrically conductive panels such that said panels in electrical contact with said electrode are electrically active when said electrode is active.

* * * * *